United States Patent [19]

Zibelin

[11] Patent Number: 4,657,545
[45] Date of Patent: Apr. 14, 1987

[54] HEART VALVE

[76] Inventor: Henry S. Zibelin, 1423 26th St., Winter Haven, Fla. 33881

[21] Appl. No.: 857,188

[22] Filed: Apr. 29, 1986

[51] Int. Cl.$^4$ ............................................... A61F 2/24
[52] U.S. Cl. ....................................................... 623/2
[58] Field of Search ............... 137/527.4, 527.6, 527.8; 251/65; 623/2

[56] References Cited

U.S. PATENT DOCUMENTS

| | | | |
|---|---|---|---|
| Re. 30,507 | 2/1981 | Kaster | 623/2 |
| 1,196,405 | 8/1916 | Steeg | 137/527.4 |
| 3,370,305 | 2/1968 | Goot | 623/2 |
| 3,476,143 | 11/1969 | Kaster | 623/2 |
| 4,417,360 | 11/1983 | Moasser | 623/2 |

*Primary Examiner*—Richard J. Apley
*Assistant Examiner*—James Prizant
*Attorney, Agent, or Firm*—William M. Hobby, III

[57] ABSTRACT

A heart valve apparatus includes a circular valve ring having a passageway therethrough and forming a valve seat around the passageway opening. A disk shaped valve element is shaped to cover the valve opening and to seat in the valve seat. The valve ring has a ring link bracket attached thereto, while the valve element has a valve element link bracket attached on one side thereof. A linkage is movably attached between the ring link bracket and the valve element link bracket to thereby allow the valve element to swing open and closed against the valve seat. The valve link has stop elements for preventing the swing of the valve link and the rotation of the valve element thereon. Two attracting permanent magnets are positioned at base of the link and valve ring to hold the valve link and valve element open until a predetermined force from pivoting valve element on the return flow, releases the link from the magnets for closing of the valve.

There are two repelling opposing magnets, one in the valve element, and one in the pivotal stop on the valve link to the valve element. These magnets have like poles facing each other, and repel each other on contact to cushion the pivoting valve element on the opening, and to allow the valve element to open fully perpendicular to valve ring, and to reduce noise, and to give the valve element a nudge into return flow for closing. The forward flow is enough to keep valve element fully open against force of repelling magnets until the reverse flow starts.

15 Claims, 18 Drawing Figures

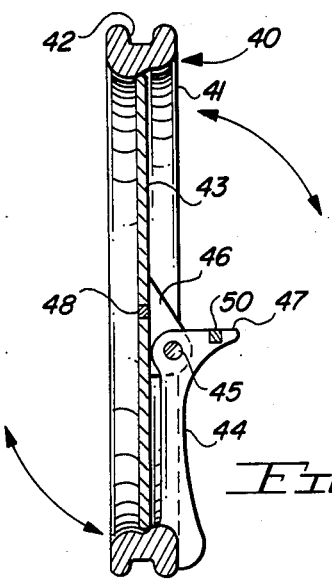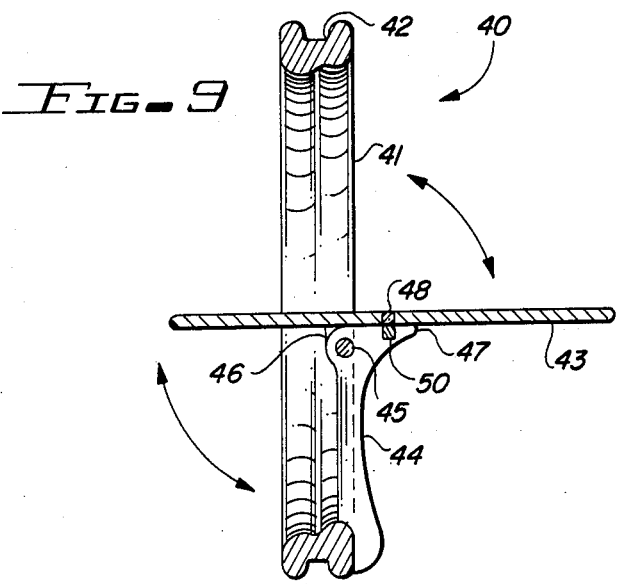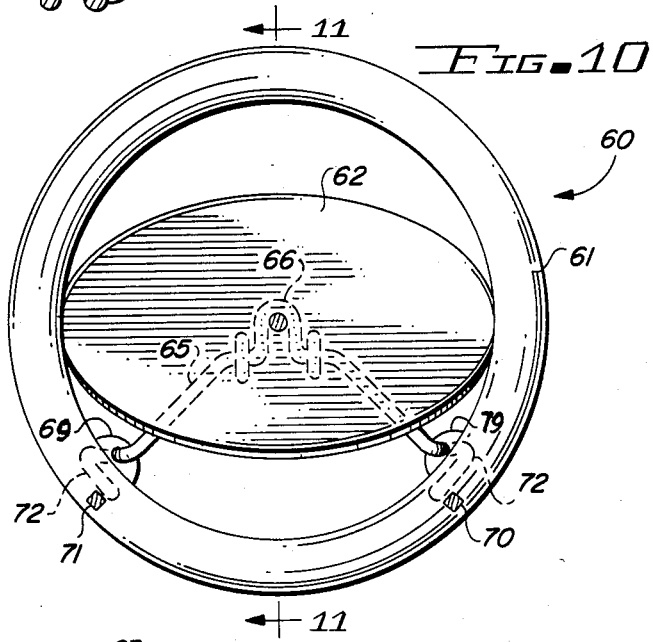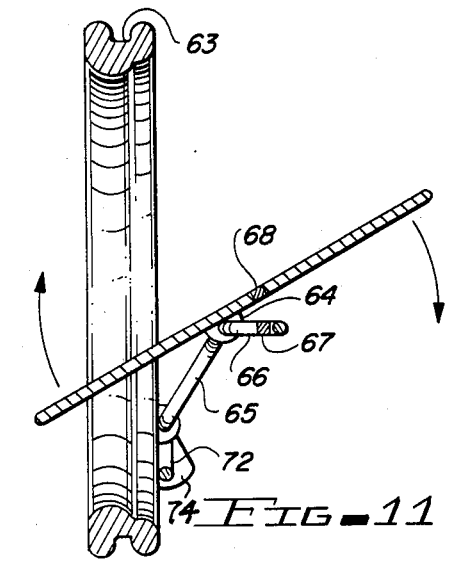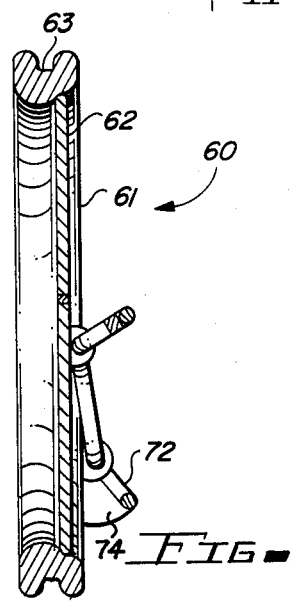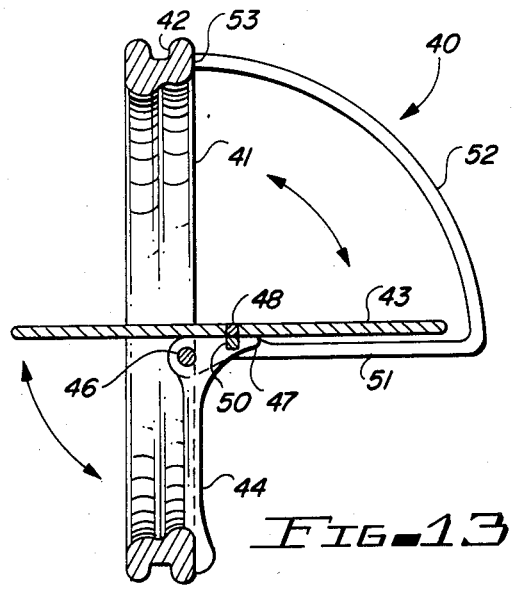

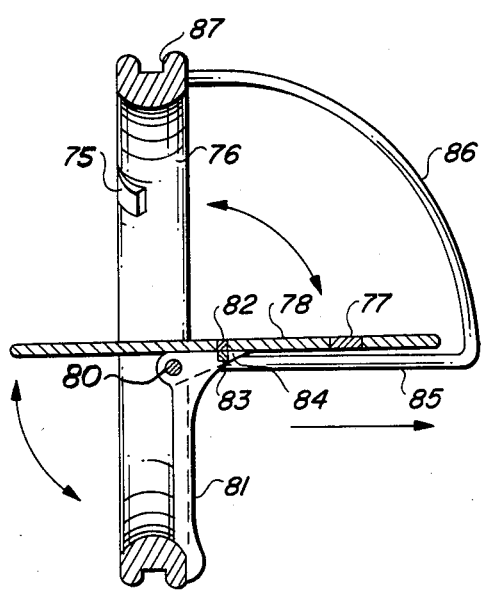
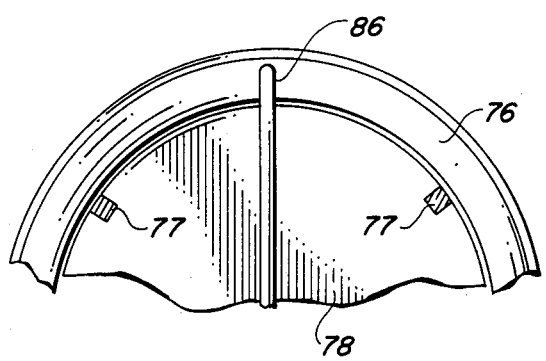
FIG.-14
FIG.-15
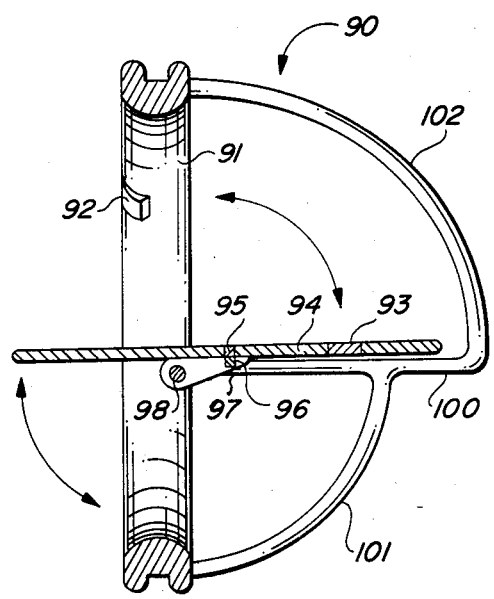
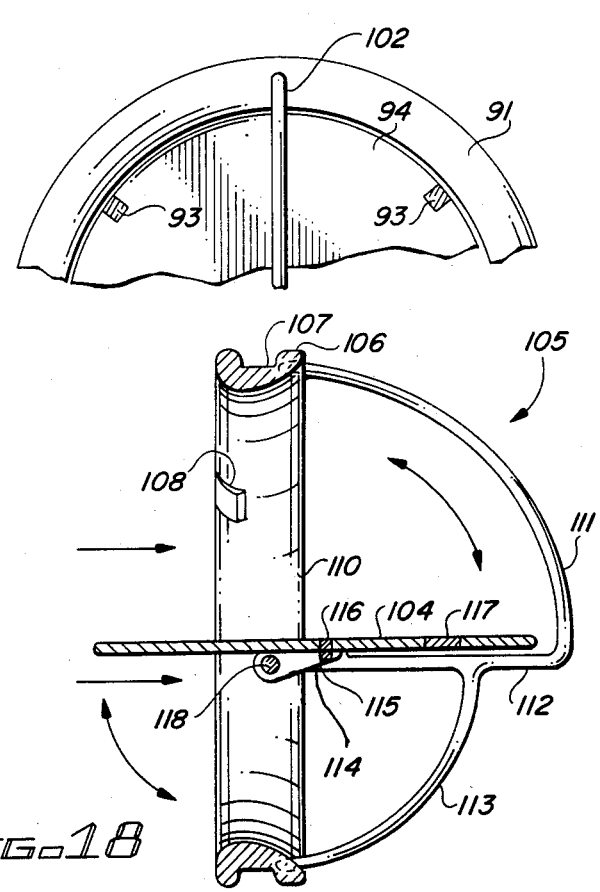
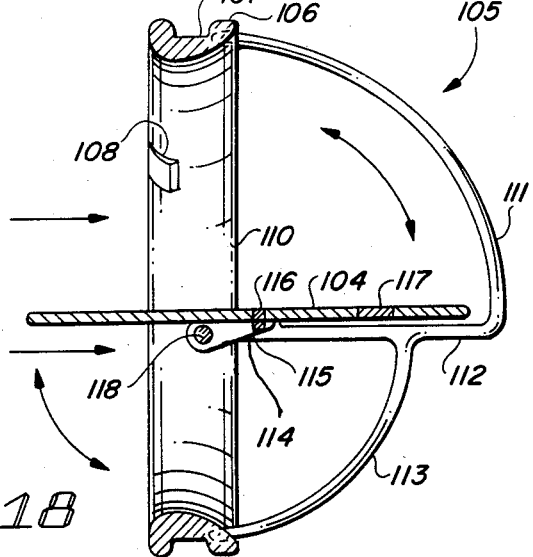
FIG.-16
FIG.-17
FIG.-18

HEART VALVE

BACKGROUND OF THE INVENTION

The present invention relates to prosthetic cardiac valves for replacement of diseased aorta valves or use in mechanical hearts.

The earliest prosthetic aortic and mitral heart valves used clinically were the ball-in-cage design, similar in design to standard check valves used with other fluids and having an attaching ring for sewing the valve into position in the patient's heart. These particular valves have been successfully used for many years. However, the disadvantages of this type of valve led to research in design of other types of valves. Two of the main disadvantages were that the relationship of a sphere or ball to the main ring diameter impeded the blood flow by the ball within the artery restricting the orifice size that could be obtained and also the disadvantages of having the cage to impede the flow of the blood. That is to say the ball has to have a diameter of between 30 and 35 percent greater than the ring to avoid impaction and in the case of a mitral valve the small ventricle which often accompanies mixed lesion of mitral incompetence and mitral stenosis, or pure calcified stenosis, the cage makes physical contact with the myocardium. This traumatizes the myocardium and contact with the interventricular septum may trigger off ectopic beats, resulting in arrhythmia which may lead to fatal ventricular fibrillation. Physical contact of the cage with the myocardium may cause the cage to lever off the sutureline which attempts to overcome this fault by selecting a smaller prosthesis may result in an excessive pressure gradient across the prosthesis.

Also in patients with a mixed valvular lesion of aortic incompetence and stenosis, or pure calcified stenosis the small annulus creates a need for a prosthetic device with an improved blood flow past the check element of the valve and with less obstruction by the cage. In order to overcome the problems with the ball-in-cage type heart valve, one of the valves developed provided a ring for attaching a sewing ring and seat for the check valve and having one or two arm extending from one or both sides of the ring with each arm having a small ring on the end thereof which bends and to be centered on the axes passing through the center of the ring and having an extension or protrusion extending through the small ring at the end of the arm for guiding the check elements in an opening an closing and to limit its movement when opening, the mitral valve having one arm extending on one side while the aorta valve having a pair of arms, one extending on either side of the main ring. The mitral valve is a generally lenticular shaped poppet element having a T-shaped protrusion extending from the center thereof through the main ring and hooked into the smaller ring with the cross or transverse portion of the T preventing the check element from escaping and limiting its movement, while the aorta check member has a protrusion from either end passing through the small rings on the end of each arm for guiding check member and limiting its movement. The check member in the aorta has a portion of a sphere less than a hemisphere for seating in the main ring and seat and a truncated cone connected to the other side. These advanced type of heart valves have generally been hand fashioned for experimental testing and the present invention relates to a method for manufacturing these advanced valves in larger quantities while reducing the overall cost and maintaining the high standards of quality necessary in a prosthetic cardiac valve.

Other types of valves for use in replacing diseased mitral and aortic valves have also been suggested in the past. For instance, it has been suggested to use various types of flaps hinged or held in various ways and adapted for flapping open and closed. These types of valves however have not been generally robust or sufficiently sturdy for more generalized use. It has also been suggested to make a toroidal check element heart valve as well as a valve formed of a resilient spirals of conical shape which are held on the annular base and overlap each other so as to form a sealed cone blockage in one direction of blood flow and angular openings in the other direction of blood flow.

Typical prior art heart valve can be seen in the following U.S. Patents:

| U.S. PAT. NO.: | INVENTOR |
| --- | --- |
| 3,601,877 | C. C. GOOSEN |
| 3,538,514 | G. SCHIMERT, ET AL. |
| 4,021,863 | A. WOIEN |
| 4,319,364 | R. L. KASTER |
| 3,825,956 | F. W. CHILD |
| 3,959,827 | R. L. KASTER |
| 4,197,593 | R. L. KASTER |

SUMMARY OF THE INVENTION

A heart valve is provided which has a circular valve ring having a passageway therethrough with a valve seat formed around the periphery of the passageway. An annular groove is formed in the outer periphery of the valve ring. The valve ring has a valve ring link bracket attached thereto for movably attaching a link to the valve ring. A valve seat is generally disk shaped to cover the main ring passageway and to seat in the valve seat formed therein. A valve element link bracket is attached to one side thereof, and has the link movably connected thereto. The heart valve link includes stops at each end to stop the rotation of the valve element in a predetermined position and to stop the rotation of the swing of the link to a predetermined position to thereby align the valve element in the proper position for the flow of blood thereby. When in an open position, permanent attracting magnets may be positioned at the base of the valve link and on the valve ring for holding the valve and the valve link in an opened position until a predetermined force against the valve element from return flow causes the link to move away from the magnetic fields to thereby give a more accurate control to the opening and closing of the valve.

There are two repelling opposing permanent magnets, one in valve element and one in pivotal stop on valve link to valve element. These magnets have like poles facing each other, and repel each other on contact. The purpose being to cushion the stop of the pivoting valve element on opening, to allow valve element to open fully (perpendicular to valve ring), to reduce noise,, and to give the valve element a gentle nudge into return flow for closing. The forward flow is enough to keep valve element open against force of repelling magnets until reverse flow starts. One embodiment has a fixed arm for the valve element to rotate or pivot upon rather than a movable link. The above paragraph applies for the operation of the valve element in this embodiment and others.

The location of the pivotal point on the valve element, helps to control the opening and closing forces on the valve element, which are in turn transmitted to the entire valve structure including valve sutures and heart itself. Proper location can also reduce noise. The closer the pivotal point to center of the valve element, the less the force. The closer to edge of the valve element, the more force generated.

A fully open valve element, with less intruding structure also reduces turbulence, and stress on valve assembly, as well as heart and attaching sutures. This allows for a more unobstructed flow of blood, with less damage to the blood cells.

On embodiment has a fixed arm for the valve element to pivot on rather than a movable link.

BRIEF DESCRIPTION OF THE DRAWINGS

Other objects, features and advantages of the present invention will be apparent from the written description and the drawings in which:

FIG. 8 is a sectional view of an alternate embodiment of a heart valve in a closed position;

FIG. 9 is a sectional view in accordance with the valve in FIG. 8 in an open position;

FIG. 10 is a front elevation of an alternate embodiment of the heart valve;

FIG. 11 is a sectional view taken on the line 11—11 of FIG. 10;

FIG. 12 is a sectional view in accordance with FIG. 11 having the valve in a closed position;

FIG. 13 is a sectional view of the valve of FIGS. 8 and 9 having the valve element open and an additional support arm;

FIG. 14 is a sectional view of another embodiment of a heart valve in an open position;

FIG. 15 is a partial elevation of the heart valve of FIG. 14 with the valve element closed;

FIG. 16 is a sectional view of yet another embodiment of a heart valve in accordance with the present invention having an open valve element;

FIG. 17 is a partial elevation the heart valve of FIG. 16 having the valve element closed; and FIG. 18 is a sectional view of another embodiment of a heart valve.

DESCRIPTION OF THE PREFERRED EMBODIMENTS

Figure 1:
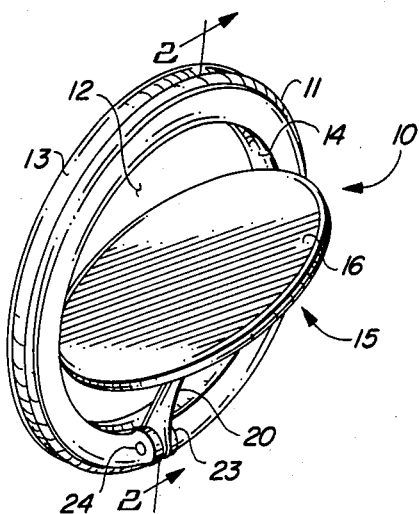
FIG. 1 is a perspective view of a heart valve in accordance with the present invention.
Figure 5:
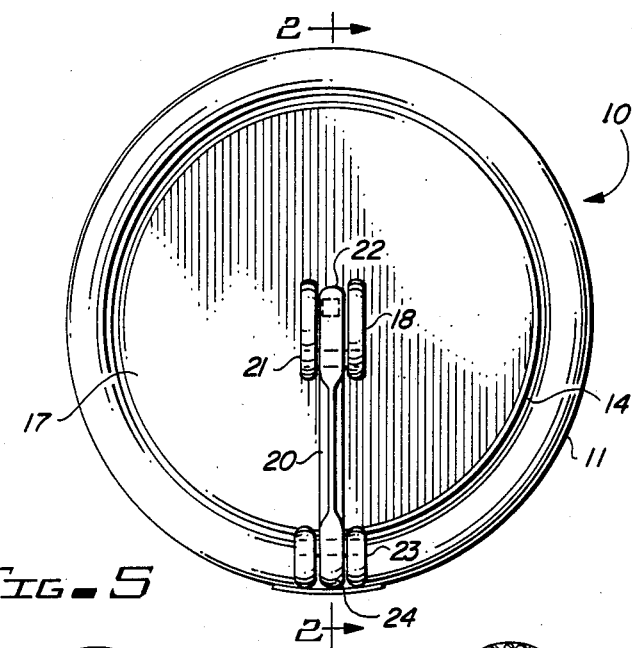
FIG. 5 is a side elevation showing one side of the heart valve in a closed position.
Figure 2:
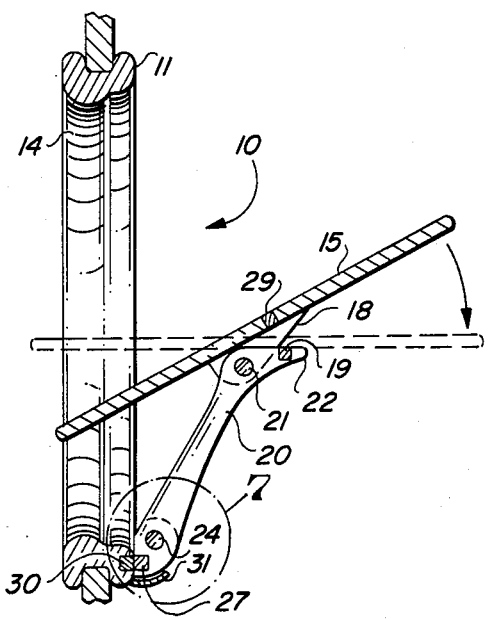
FIG. 2 is a sectional view taken on the line 2—2 of FIG. 1.

Referring to FIGS. 1 through 7 of the drawings, a heart valve 10 is illustrated having a main valve ring 11 having a passageway 12 through the center thereof and having an annular groove 13 around the outer periphery of the ring 11 filled with a suturing material 32 for use in attaching the artificial heart valve to a patient's heart. The passageway 12 through the valve ring 11 has a valve seat 14 formed on the inner periphery of the passageway for the seating of the valve element 15. The valve element 15 has a disk shape having a smooth front side 16 and a smooth rear side 17 with the rear side having a valve element link bracket 18 fixably attached thereto. The valve element link bracket 18 has a valve link member 20 attached thereto with a pin 21. The stop 22 has a magnet 19 mounted therein and coacting with the opposite magnet 29 mounted in the valve element 15. The link member 20 has a stop 22 extending therefrom for stopping the rotation of the valve element 15 on the pin 21. The valve element 15 moves from a closed position into alignment with the flow of blood through the valve passageway. To a full open position as indicated by the broken line depiction in FIG. 2. The valve linkage 20 is aerodynamically shaped for a streamline flow of blood thereby and is connected to a valve ring link bracket 23 by a pin 24. The link bracket 23 is fixably attached to the valve ring 11 and allows a swinging of the valve link 20 responsive to the blood pressure differential on the valve element 15. The link has a second stop surface 25 attached on an extension to the link for stopping the rotation of the link 20 against the magnet 30 mounted on the surface 26 of the valve ring 11. In addition, the valve link 20 has a permanent magnet 27 mounted therein to form the stop surface and to produce a magnetic field acting on the surface 26 along the valve ring 11. It will, of course, be clear that the magnets placed on the ring and on the link as illustrated in the drawings having different poles facing each other. The magnets 27 and 30 through their magnetic fields, will tend to hold the linkage 20 in an open position, as shown in FIG. 2 until sufficient pressure differential is applied to the valve element 15 to force the valve link 20 and valve element 15 back towards a closed position. Thus the weak magnets 27 and 30 slightly delays a return action of the valve element 15 and makes it happen in a more uniform poppet type action. A shield 31 is placed adjacent the linkage 20 connection and attached to the ring 11.

Figure 3:
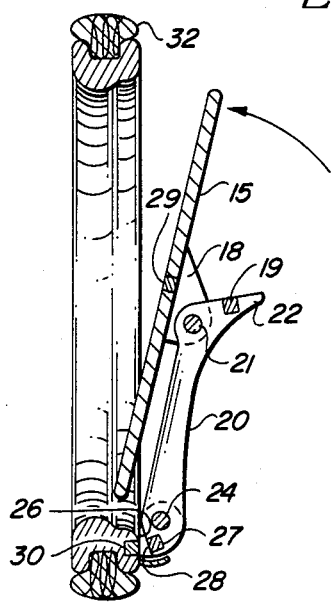
FIG. 3 is a sectional view as shown in FIG. 2 with the valve in a different position.
Figure 4:
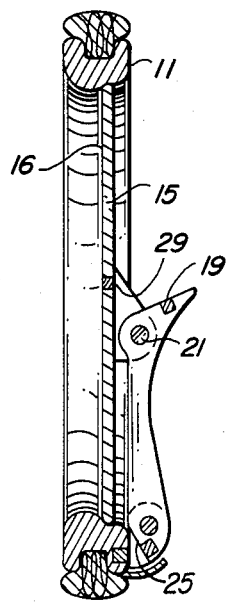
FIG. 4 is a sectional view of the valve element of FIGS. 2 and 3 shown in a closed position.

In operation, the valve will be in its closed position as shown in FIG. 4 with a valve element 15 against the valve seat 14, to close off the flow of blood through the passageway 12. When the direction of the flow of the blood is pumped against the front side 16 of valve element 15, the pressure differential between the sides 16 and 17 of the valve element 15 forces the valve element to move open by rotating the link 20 on the pin 24 and by rotating the valve 15 on the pin 21 as shown in an intermittent position in FIG. 3.

FIG. 2 shows the valve element in a fully open position in broken lines with permanent magnets 27 and 30 stopping the further movement of the link 20 and providing a holding force for the valve element in an open position. As shown by broken lines, the valve element 15 is held in a fully open position by the flow of blood through the opening 12. When the direction of flow and the pressure differential changes on the valve element 15. The repelling force of magnets 19 and 29 nudges valve element into reverse flow and it rotates the valve element 15 as shown in FIG. 3 and forces the separation of the magnets 27 and 30 away from the stop surface to pull the link 20 to rotate until the valve element 15 seats on the valve seat 14.

Turning to FIGS. 8 and 9 a second embodiment of a heart valve 40 is illustrated, having a main valve ring 41 forming a passageway therethrough and having an annular groove 42 extending around the outer periphery of the ring 41 for insertion of suturing material for use in attaching a heart valve to a patient's heart. The valve element 43 is attached to a streamlined support arm 44 which in turn is fixably attached to the ring 41. The valve element 43 is attached to the arm 44 with a pin 45 and is adapted to rotate thereon from a closed valve position as shown in FIG. 8 to a fully opened valve position as shown in FIG. 9. The valve element 43 rotates on the pin 45 which is connected to a bracket 46 attached to the valve element 43 until the valve element 43 abuts against a stop surface 47 on the arm 44. Opposing permanent magnet 48 on the valve element 43 and magnet 50 on the arm 44 are attached to have their faces of like magnetic polarity to each other, so that the magnets repel each other and nudge the valve element 43 into reverse flow for closing. In FIGS. 8, 9 and 13 there is no valve seat in the small area on either side of the valve ring where the valve element pivots. After the heart pumps the blood through the valve 40 in it's open position in FIG. 9, the blood will tend to reverse its flow as the heart returns from the pumping action and the valve element 43 will shut, blocking the return flow and will again work with a pop it type action because of the repelling action of the magnets 48 and 50.

FIG. 13 shows a slightly modified embodiment of the valve of FIGS. 8 and 9 in which the artificial heart valve 40, ring 41 having the groove 42 and the arm 44 has the rotating valve element 43 which is disk shaped and rotates on the pin 46. The arm 44 stop portion 47 has an extension arm 51 extending parallel to the opened valve element 43 and then in an upwardly extending arm portion 52 welded at 53 to the valve ring 41. This embodiment also has the magnets 48 and 50 as shown in FIGS. 8 and 9 and performing the same function.

Turning to FIGS. 10, 11 and 12, another embodiment of an artificial valve 60 has a main valve ring 61, having a valve element 62 operating in connection therewith. The valve ring 61 has an annular groove 63 as in the other embodiments, but the disk shaped valve element 62 has an eye bracket 64 formed thereon and connected into a supporting linkage 65. The supporting linkage 65 is attached to supporting brackets 69 and 79 attached to the ring 61 forming a generally triangular shaped support bracket 65 having a loop 66 formed thereon. Opposing magnets 67 and 68 are placed on the bracket loop portion 66 and on the disk 62 respectively with their faces having an like polarity for repelling each other and returning the disk 62 into reverse flow for closing sequence. The unit may also have a pair of magnets 70 and 71 attached to the ring 61 for attracting and holding the extending arms 72 on the support arm 65 and extending through the arm support bracket 69 and 79. FIGS. 10 and 11 show the embodiment with partially opened valve element 62, while FIG. 12 shows the valve element 62 in a closed position forming a seal with the ring 61.

Figure 6:
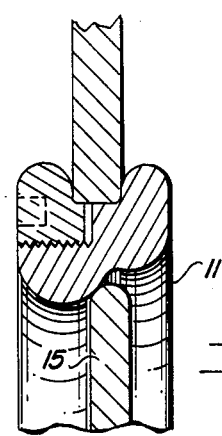
FIG. 6 is a partial sectional view of a portion of the valve ring and valve element showing adaptation for mechanical heart.
Figure 7:
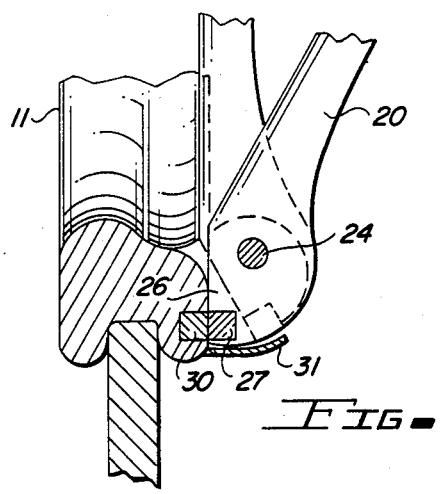
FIG. 7 is a partial sectional view taken on the circle 7 of FIG. 2.

The heart valve in accordance with the present invention is attached in a conventional manner and may have synthetic fabric 32 of FIG. 3 attached to form a seat in the groove 13 of the valve ring 11 for attaching to heart tissue and adaptation as in FIG. 6 for attaching to mechanical heart. There are also shields 74 beside extending arms 72.

Referring to FIGS. 14 and 15, another embodiment of a heart valve in accordance with the present invention is illustrated having a valve ring 76 with a pair of repellings magnets 75 attached thereto. The magnets 75 acts as a valve seat for the valve element 78 which pivots on a pin 80 attached to a support arm 81 which in turn is attached to the valve ring 76. The valve element 78 has a pair of repelling magnet 77 attached thereinto, and a repelling magnets 82 attached thereinto mounted to be pushed against a repelling magnet 83 mounted in a bracing arm portion 84 of the support arm 81. This embodiment has a support arm 85 extending from the support arm 81 in an upwardly arcuate arm 84 continuing from the arm 85 and attached to the valve ring 76. This embodiment also has the annular groove 87 used in attaching the heart valve.

As seen in FIG. 15, the repelling magnets 77 on the valve element 78 utilizes two spaced magnets 77 positioned to be adjacent to a pair of repelling magnets 75 on valve ring 76 when the valve is in a closed position, as in FIG. 15.

Referring to FIGS. 16 and 17, a heart valve 90 is illustrated having a valve ring 91, having a pair of repelling magnets 92 mounted thereon for coacting with a pair of repelling magnets 93 mounted to the valve element 94, similar to the embodiment of FIGS. 14 and 15. This embodiment also has a repelling magnet 95 attached to the valve element 94 coacting with a repelling magnet 96 attached to a valve element support arm 97 having a pin 98 thereon for pinning the valve element 94 thereto. The support arm 97 is supported with a horizontally extending arm 100 supported on one side by an arcuate downwardly extending arm 101 attached to the valve ring 91 in an upwardly extending arcuate support arm 102 attached to the top portion of the valve ring 91. This heart valve can be seen to be similar to the one in FIGS. 14 and 15, except for the supporting arm 84 being attached by a pair of arcuate arms 101 and 102 extend upwardly and downwardly rather than having a vertically extending support arm 81 as in FIG. 14. It should also be noted that the embodiments of FIGS. 14 and 15 and of FIGS. 16 and 17, have a valve ring which is smooth with no seat and contributes to the smooth flow with no damage to the blood on closing. The opposing and repelling magnets in each embodiment cushions the opening and closing of the valve element, but allows the valve element to open fully, to thereby reduce resistance and turbulence as would be caused by a partially open valve element. The repelling magnets also assist in reducing noise, shock and stress on components of the valve, as well as the sutures and the heart of the patient. The pivotal point 80 and 98 are located on the valve element for opening and closing and valve element in a manner to control the forces thereon and to also reduce damage to the blood as well as noise, shock and stress on the heart, suturing and shock and stress on the valve components.

Turning to FIG. 18, an embodiment of a heart valve 105 is illustrated in a sectional view and is similar to the embodiment shown in FIGS. 16 and 17 except the ring 106 has a sloping angle 110 between the front and back of the ring 106. The ring 106 inherently creates a venturi, but the drop off of the angle 110 reduces the velocity of the flow to thereby reduce pressure on the exit side of the valve 105 to soften the impact of blood against the valve element support structure which reduces possible damage to blood and the formation of thrombi or clots. The valve ring 106 has an annular groove 107 along with a pair of magnets 108, similar to that shown in FIGS. 14 thru 17, which coacts with the magnets 117 in the valve element 104. The ring 106 has a horizontal arm 112 supported by an arcuate upwardly extending arm 111 and a lower extending arm 113 with arms 111 and 113 being attached to the ring 106 at opposite sides thereof. The horizontal arm 112 has a valve element supporting pivoting arm 114, having a magnet 115 mounted therein for coacting with a repelling magnet 116. The valve element 104 rotates on the pin 118 and operates in the same manner as the valve of FIGS. 16 and 17, except for the change in the slope 110 in the ring 106.

It should be clear at this point that a heart valve has been illustrated which provides improved action based on the compound movement of the valve element as well as the utilization of permanent magnets to give a more accurate control of the opening and closing of the valve element. However, the present invention is not to be construed as limited to the forms shown which are to be considered illustrative rather than restrictive.

I claim:

1. A heart valve comprising in combination:
   a circular valve ring having a passageway therethrough and forming a valve seat around the periphery of the passageway therethrough;
   a disk shaped valve element shaped to cover the passageway through the valve ring and to seat in the valve seat formed therein;
   a valve element link bracket fixably attached to one side of the valve element;
   a valve link member movably attached to said valve element link bracket; said valve link member having a magnet formed in one end portion thereof;
   a valve ring link bracket fixably attached to said valve ring and having said link movably attached thereto; whereby said valve element can move on said link member and said link member can move on said ring during the opening and closing of said valve element; and
   said circular valve ring having a valve link member attaching bracket formed thereon for movably supporting the valve link member thereto.

2. A heart valve in accordance with claim 1 in which said circular valve ring has a slope formed therein from one side of the ring to the other, thereby providing a drop-off in the velocity of the flow of fluid therethrough.

3. A heart valve in accordance with claim 1 in which said circular valve ring has an annular groove therearound and suturing material formed therein for attaching the heart valve to a patient.

4. A heart valve in accordance with claim 1 including a heart valve link shield attached to said circular valve ring adjacent connecting means connecting said valve link member to said circular valve ring.

5. A heart valve in accordance with claim 3 in which the circular valve ring has a magnet formed therein facing the magnet attached to said valve link member and having an opposite magnetic polarity forming the magnet in said valve link member, whereby said magnets can attract and hold one to the other in one position.

6. A heart valve in accordance with claim 5 in which said valve link member has a second magnet therein.

7. A heart valve in accordance with claim 6 in which said disk shaped valve element has a magnet formed therein and positioned adjacent to the second magnet formed in said valve link member when said disk shape valve element is in an open position and said magnets having facing like polarities opposite to each other for repelling said disk shape valve element to return the valve element into the return flow to partially close the valve.

8. A heart valve in accordance with claim 4 in which said valve link member has a stop surface formed thereon for stopping the rotation of said disk shaped valve element thereon.

9. A heart valve in accordance with claim 8 in which said link member has a second stop surface for stopping the rotation of said valve link member on said circular valve ring in one position.

10. A heart valve comprising in combination:
    a circular valve ring having a passageway therethrough and forming a valve seat around the periphery of the passageway therethrough;
    a disk shaped valve element shaped to cover the passageway through the valve in one position and to seat in the valve seat formed therein and to rotate from said one position to a second position;
    a valve element support arm fixedly attached to said circular valve ring and having said valve element rotably attached thereto for rotating thereon; and
    magnetic means for repelling said disk shaped valve element and moving said valve element into the return flow for closing said magnetic means including a permanent magnet mounted in said disk shape element and a second permanent magnet mounted in said disk shape valve element support arm, said magnets having the same polarity facing each other and being juxtaposed adjacent each other in one position for repelling said disk shaped valve element and moving the valve element into return flow for closing.

11. A heart valve in accordance with claim 10 in which said disk shaped valve element has a bracket attached to one face thereof and said valve support arm has a connecting pin to rotably connect said valve element to said valve element support arm.

12. A heart valve in accordance with claim 10 in which said valve element support arm fixably attached to said circular valve ring include a horizontal arm, having said disk shape valve element rotably attached thereto and an arcuate arm attaching said horizontal arm to said circular valve ring.

13. A heart valve in accordance with claim 10 in which said circular valve ring has a slope formed therein from one side of the ring to the other, thereby providing a drop-off in the velocity of the flow of fluid therethrough.

14. A heart valve in accordance with claim 11 including an annular groove formed around said circular valve ring for insertion of suturing material for attaching said heart valve to a patient.

15. A heart valve in accordance with claim 16 in which said valve element support arm includes a second arcuate arm attached to said horizontally extending arm and attached to said circular valve ring thereby supporting said horizontal arm in the upper and lower portions of said valve ring.

* * * * *